United States Patent [19]
Wolf

[11] Patent Number: 6,163,726
[45] Date of Patent: Dec. 19, 2000

[54] SELECTIVE ABLATION OF GLANDULAR TISSUE

[75] Inventor: Gerald L. Wolf, Winchester, Mass.

[73] Assignee: The General Hospital Corporation, Boston, Mass.

[21] Appl. No.: 09/158,949

[22] Filed: Sep. 21, 1998

[51] Int. Cl.$^7$ ...................................................... A61F 2/00
[52] U.S. Cl. ............................ 607/101; 607/156; 606/33; 606/34
[58] Field of Search .................................... 607/101, 102, 607/154–156; 606/33, 34

[56] References Cited

U.S. PATENT DOCUMENTS

| | | | |
|---|---|---|---|
| Re. 32,066 | 1/1986 | Leveen | 128/804 |
| 5,251,645 | 10/1993 | Fenn | 607/154 |
| 5,441,532 | 8/1995 | Fenn | 607/101 |
| 5,531,662 | 7/1996 | Carr | 600/2 |
| 5,540,737 | 7/1996 | Fenn | 607/101 |

(List continued on next page.)

FOREIGN PATENT DOCUMENTS 0 804 900 A1  11/1997  European Pat. Off. .

OTHER PUBLICATIONS

Burdette et al., "Electromagnetic and Acoustic Properties of Tissues," *Physical Aspects of Hyperthermia*, G.H. Nussbaum, Ed., AAPM Medical Physics Monographs, 8:105–150, 1982.

Chaudhary et al., "Dielectric Properties of Normal & Malignant Human Breast Tissues at Radiowave & Microwave Frequencies," *Indian Journal of Biochemistry & Biophysics*, 21:76–79, 1984.

Farase et al., "An automated method for mapping human tissue permittivities by MRI in hyperthermia treatment planning," *Phys. Med. Biol.*, 42:2159–2174, 1997.

Fenn, "Evaluation of Adaptive Phased Array Antenna Far–Field Nulling Performance in the Near–Field Region," *IEEE Transactions on Antennas and Propagation*, 38:173–85, 1990.

Fenn et al., "Improved Localization of Energy Deposition in Adaptive Phased–Array Hyperthermia Treatment of Cancer," *Lincoln Laboratory Journal*, 9:187–96, 1996.

Foster et al., "Dielectric Properties of Tumor and Normal Tissues at Radio through Microwave Frequencies," *Journal of Microwave Power*, 16(2):107–119, 1981.

Geise et al., "Composition of Mammographic Phantom Materials," *Radiology*, 198:347–70, 1996.

Hassan et al., "Decreased Apoptosis in Non–Involved Tissue from Cancer–Containing Breasts," *Journal of Pathology*, 184:258–64, 1998.

Joines et al., "The Measured Electrical Properties of Normal and Malignant Human Tissues from 50 to 900 MHz," *Medical Physics*, 21:547–550, 1994.

Kolb et al., "Occult Cancer in Women with Dense Breasts: Detection with Screening US—Diagnostic Yield and Tumor Characteristics," *Radiology*, 207:191, 1998.

Mallard et al., "Dielectric Absorption of Microwaves in Human Tissues," *Nature*, 213:28–30, 1967.

Miller–Catchpole, "Diagnostic and Therapeutic Technology Assessment (DATTA)," *JAMA*, 271:797–802, 1994.

(List continued on next page.)

*Primary Examiner*—John P. Leubecker
*Assistant Examiner*—David M. Ruddy
*Attorney, Agent, or Firm*—Fish & Richardson P.C.

[57] ABSTRACT

The invention features a method for selectively ablating tumor-forming, glandular tissue in a breast by exposing the breast to microwave radiation that ablates glandular tissue while avoiding damage to the fatty tissues of the breast.

20 Claims, 9 Drawing Sheets

U.S. PATENT DOCUMENTS 5,662,110  9/1997  Carr ..................................... 128/653.1
5,704,355  1/1998  Bridges ................................. 607/101

OTHER PUBLICATIONS

Panjehpour et al., "Nd: YAG Laser Hyperthermia Treatment of Rat Mammary Adenocarcinoma in Conjunction with Surface Cooling," *Lasers in Surgery and Medicine,* 11:356–362, 1991.

Prionas et al., "Temperature distribution induced in pig tissues by a water–cooled disk electrode rf system" *American Physics,* 11:22–25, 1984.

Robinson et al., "Interstitial Laser Hyperthermia Model Development for Minimally Invasive Therapy of Breast Carcinoma," *J. Am. Coll. Surg.,* 136:284–292, 1998.

Surowiec et al., "Dielectric Properties of Breast Carcinoma and the Surrounding Tissues," *IEEE Transactions on Biomedical Engineering,* 35:257–63, 1982.

SELECTIVE ABLATION OF GLANDULAR TISSUE

FIELD OF THE INVENTION

The invention relates to the selective ablation of glandular tissue using microwave radiation.

BACKGROUND OF THE INVENTION

Breast tissue is composed of glandular tissues specialized for lactation, and a connective tissue stroma containing blood vessels, adipose tissue, nerves, and lymphatic tissue. Breast tissue is bounded by the skin. About 90% of all breast cancers originate in the lactiferous ductal tissue of the breast, with the remaining 10% beginning in the glandular tissue lobules.

Recent estimates indicate that breast cancer will develop in about twelve percent of women in the United States during their lifetimes. The risk of developing breast cancer increases with the age of a woman. In addition, inherited and environmental factors can increase the risk for breast cancer. One way a woman can minimize her risk for developing breast cancer is to have one or both breasts removed by a prophylactic mastectomy. This method is disadvantageous because of its attendant discomfort and disfigurement.

SUMMARY OF THE INVENTION

The invention is based on the discovery that microwave radiation can be used to selectively ablate ductile and glandular tissue of the breast while not affecting fatty tissues and skin of the breast. Thus, the ductile and glandular tissues which could give rise to tumors in the breast can be selectively destroyed with little discomfort, while the appearance of the breast is preserved.

In one aspect, the invention features a method for preventing the development of a breast tumor in an individual by identifying an individual at risk for developing a breast tumor and irradiating with microwave radiation a region of the breast at risk for developing the tumor at a wavelength and for a time sufficient to heat glandular tissue but not fatty tissue to a temperature of at least about 43° C. The microwave radiation thus prevents the development of a breast tumor in the glandular tissue.

"Glandular tissue" includes both lactiferous ductal tissue and glandular tissue.

The microwave radiation can be between 100 and 1000 Mhz, 500 and 100 MHz, 902 and 928 MHz, or about 915 MHz. In some embodiments, the microwave radiation forms a focused field in the tissue. In some embodiments, the individual may lack an identifiable tumor in the tissue.

In another aspect, the invention includes a method for selectively ablating glandular tissue, by ablating substantially all of the glandular tissue of a breast with microwave radiation, wherein the radiation ablates glandular tissue but not fatty tissue of the breast.

In some embodiments, the glandular tissues include tumorous tissue. In other embodiments, the glandular tissue may lack any detectable tumor. A "detectable tumor" is a tumor that is 3 mm or greater in diameter.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Among the advantages of the present invention are that it allows for the destruction of malignant and premalignant glandular tissues in a manner that is minimally invasive. The remaining breast tissues are spared. Thus the method produces a cosmetically superior result with far less pain and discomfort in comparison with prophylactic or therapeutic regimens such as the various forms of mastectomy or lumpectomy, along with adjuvant therapies. In addition, removal of tumor-forming breast tissues using the methods of the invention can obviate the need for adjuvant radiation or chemotherapy and its associated costs, which are often used in combination with mastectomies or lumpectomies.

Other features and advantages of the invention will be apparent from the following detailed description, and from the claims.

DETAILED DESCRIPTION

Figure 1:
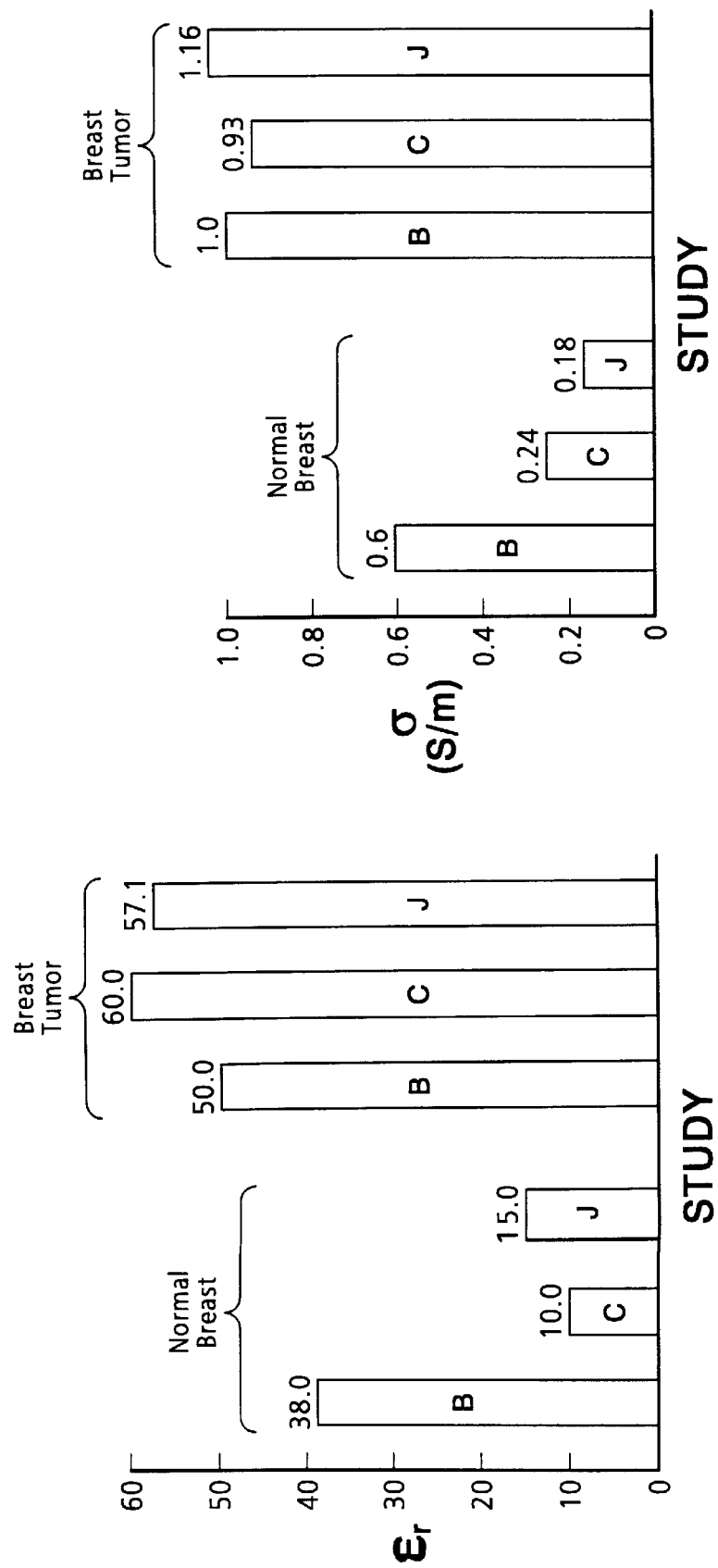
FIGS. 1A and 1B are histograms comparing relative dielectric constant (1A) and electrical conductivity (1B) values for normal and tumorous breast tissue following exposure to 915 MHz microwave radiation.

The present invention provides a method for selectively ablating glandular tissues of the breast, which are the tissues in which breast carcinomas develop, while preserving the fatty tissues of the breast. The glandular tissues of the breast include alveoli and ducts, which comprise a cell population that is water-rich. The remainder of the breast volume is composed of skin and adipose tissue. The adipose tissue is composed mostly of liquid fat and has a low water content. The new methods are most effective in cases in which the patient has a relatively high amount of fatty breast tissue.

The relative contribution of fatty and water-rich tissues in the breast can be determined using any of several methods known in the art. For example, the composition of breast tissue can be determined by analysis of breast tissue specimens. However, this method is relatively laborious and may be nonrepresentative because of sampling errors or artifacts arising in processing the specimens. An alternative method for determining the composition of breast tissue is radiographic imaging. This technique visualizes water-rich tissues separately from fatty tissue and is based on differences in x-ray attenuation in the two types of tissues. The effective glandular content of the average breast has been determined to be about 34%, with glandular content being higher in small breasts than in large breasts (Giese et al. Radiology 198:347–70, 1996; Hassan et al., J. Pathology 184:258–64, 1998). In addition, the age of the patient, e.g., a woman, as well as hormonal influences, can influence the relative abundance of glandular and fatty tissues in the breast (Kolb et al., Radiology 207:191, 1998).

The ratio of glandular and fatty tissue within the breasts depends on three main factors: (1) genetic predisposition; (2) the ratio of total body fat to total body weight; and (3) age. Thus, tissue within the breast can vary widely, from being composed of primarily fatty tissue to primarily dense glandular (high-water content) tissue. Typically, at an age of about 40 years or less, the female breast tends to be very dense. As age increases over 40 years, the female breast tends to become less dense and more fatty.

When tissues of the breast are exposed to microwave energies, heating occurs predominantly by inducing rapid oscillations of water molecules. The differential sensitivity of water-rich and fatty breast tissue to microwave radiation can be expressed in terms of their respective dielectric constants and electrical conductivities. High dielectric constants and conductivities correlate with more rapid heating upon microwave radiation.

Dielectric constants and conductivities for glandular and fatty tissues of the breast can be extrapolated from published values for normal breast tissue and cancerous breast tissue, e.g., as described in Burdette et al., Physical Aspects of Hyperthermia, G. H. Nussbaum, Ed., AAPM Medical Physics Monographs 8:105–150, 1982, Chaudhary et al., Indian J. Biochem. Biophys. 21:76–79, 1984, Joines et al., Med. Phys. 21:547–550, 1994, and Surowiec et al., IIEEE Transactions Biomed. Eng. 35:257–63, 1982.

FIGS. 1A and 1B show a comparison of the relative dielectric constant and electrical conductivity of normal breast tissue and breast tumor tissue following irradiation with 915 MHz microwave radiation using the data of Burdette et al. ("B"), Chaudhary et al. ("C") and Joines et al. ("J"). The comparison reveals that tumor tissue has a higher relative dielectric constant relative to normal breast tissue (FIG. 1A) as well as higher electrical conductivity (FIG. 1B).

Electric properties of breast tissue upon irradiation at about 915 MHz were then compiled using the data of Chaudhary and Joines. The average dielectric constant of normal breast at 915 MHz is 12.5 and the average conductivity is 0.21 S/m. In contrast, for breast tumor the dielectric constant is 58.6 and the average conductivity is 1.03 S/m. The dielectric parameters of normal breast and breast tumor are similar to fatty tissue and high-water content muscle tissue, respectively. However, it is possible that the normal breast tissue in these studies is a mixture of glandular and fatty tissue. Thus, the actual dielectric constant and conductivity of fatty tissue may be lower than suggested from these studies.

Data obtained by Baudette et al. (e.g., in FIGS. 1A and 1B) were omitted in electric property calculations because they are based on measurements taken through the skin and may not accurately reflect the properties of breast tissue itself. The data of Surowiec et al. were also omitted because they measured parameters in the range 20 kHz to 100 MHz, and it is not possible to accurately predict the electrical properties of breast tissues at 915 MHz from data measured at 20 kHz to 100 MHz frequencies.

Because fatty tissue has a lower dielectric constant and lower average conductivity relative to glandular tissue, the fatty tissue is heated less than glandular tissue. Normal, water-rich breast glandular tissue can thus be destroyed by microwave heating while fatty tissues remain unaffected. Carcinomas are even more sensitive to microwave radiation and are also selectively ablated.

In women without a glandular neoplasm, but who are at risk for developing breast cancer, the new methods significantly reduce or eliminate breast cancer without significantly affecting the overall appearance of the breast. In women with focal or diffuse neoplasm, including carcinoma in situ, the methods selectively ablate neoplastic, dysplastic, and premalignant glandular tissues.

In some embodiments, microwave radiation is used to selectively ablate glandular tissue using adaptive phased array technology as described by Skolnik, Introduction to Radar Systems 2 ed., McGraw-Hill, 1980; Adaptive Antennas, Concepts and Performance, Prentice Hall, N.J., 1988; and Fenn, IEE Transactions on Antennas and Propagation 38:173–85, 1990. An adaptive phased array hyperthermia system uses E-field feedback measurements to focus its energy on deep tissue while simultaneous nullifying any energy that might overheat surrounding tissue. Adaptive microwave phased arrays can deliver heat to tissues deep within the breast, while avoiding, or minimizing, undesired heating of the breast's superficial tissues. In addition, the focused microwave field does not substantially damage fatty tissue in the zone in which the radiation is applied. Focused radiation is also applied so as to avoid undesired heating of the skin. Thus, focused irradiation avoids undesired "hot spots" that can damage non-target breast tissue and tissues surrounding the breast tissue, such as muscle and skin.

Apparatus for Selectively Ablating Glandular Tissue of the Breast Using Focused Microwave Fields Arrays for applying focused microwaves are described in U.S. Pat. Nos. 5,251,645; 5,441,532; U.S. Patent No. 5,540,737, and Fenn et al., Lincoln Laboratory Journal 9:187–96 (1996). The monopole phased array system described in U.S. Pat. No. 5,540,737 can be adapted for use in the prophylactic methods described herein.

Figure 2:
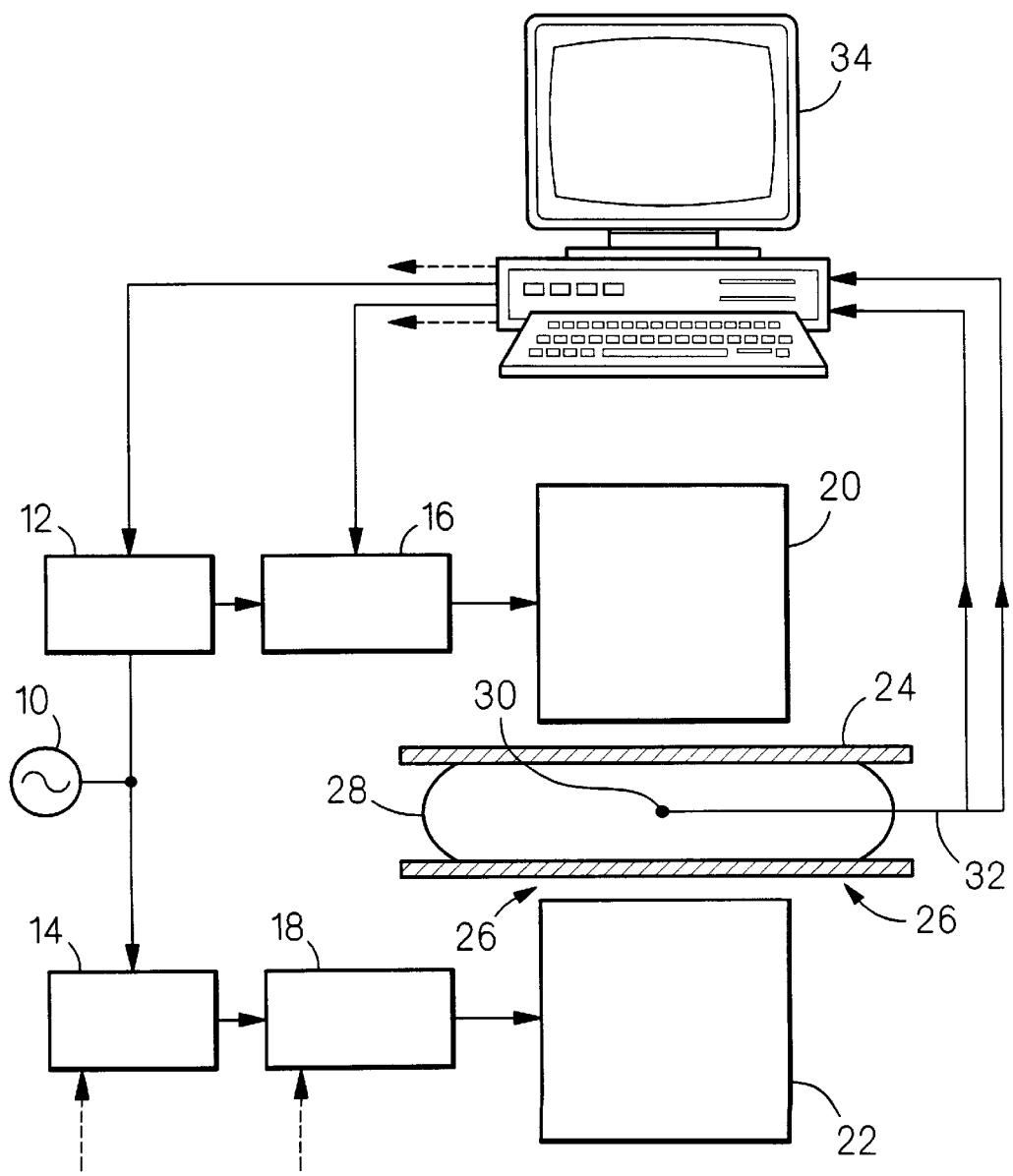
FIG. 2 is a schematic diagram showing an apparatus for selectively ablating glandular tissue.

To heat tissues reliably at microwave frequencies, the tissue to be heated is surrounded with two or more coherent applicators controlled by an adaptive phased array algorithm as described above. An apparatus to ablate glandular and ductal tissue and tumors in intact breast using an adaptive microwave phased array hyperthermia system is shown in FIG. 2. The system includes a microwave source 10, which transmits microwaves through phase shifters 12 and 14 to power amplifiers 16 and 18 and on to microwave waveguide applicators 20 and 22. Microwave radiation is delivered from the applicators 20 and 22 through two compression plates 24 and 26 to a target breast tissue 28 placed between the compression plates 24 and 26. The radiation is focused to a region 30 in the breast tissue. Typically, the breast is compressed to a thickness of 4–8 cm, and the microwave applicators are separated from the compression plates by an air gap of 2–3 mm. The applicators focus microwave radiation at a point midway between them.

A probe 32 monitors the temperature and field strength, and this information is conveyed to a computer 34, which adjusts the input microwave radiation delivered through the phase shifters 12 and 14 and power amplifiers 16 and 18. An example of a commercially available apparatus that can be used for focused microwave ablation is the Celsion Microfocus 1000 System (Celsion Corp., Columbia, Md.).

Air-cooled waveguide apertures are preferably used to provide a heating pattern that can heat large volumes of glandular, ductal, and tumor tissue. Because high-water content tissue and fatty breast tissues have different dielectric parameters at 915 MHz, the high-water content glandular and ductal tissues heat more rapidly than the fatty breast tissue. High-water content tissue will therefore be ablated under conditions in which fatty tissue is spared.

Microwave irradiation is preferably performed on a compressed breast, which reduces the depth to which microwaves must penetrate the breast tissue.

Methods for Selectively Ablating Glandular Tissue of the Breast

The new methods can be used prophylactically on individuals not known to have cancerous breast tissue and who have no detectable tumor. The new methods can also be used therapeutically, e.g., on women who have signs of cancer. Methods of identifying women at risk for breast cancer are known in the art. In some cases, a woman at risk for breast cancer will be one who has a familial history of breast cancer, e.g., a member of a family having mutations in the BRCA1 or BRCA2 genes, or an individual with Li-Fraumeni syndrome. In other cases, a woman is considered at risk because the disease has occurred in one or more family members, even though no genetic lesion for breast cancer has been identified in the individual's family. A woman may also be at risk because she has been exposed to risk factors, e.g., environmental, nutritional, or hormonal factors, associated with the development of breast cancer. Alternatively, a woman may be at risk with respect to one breast because a neoplasm has been identified in glandular tissue of the other breast. The new methods can also be used on individuals who have a morbid fear of developing breast cancer, or have galactorrhea, which is characterized by the discharge of milk from the breasts of non-pregnant women. The new methods can also be used on men who have, or may be predisposed to, any of the above-conditions, or who have gynecomastia.

The apparatus described above can be used to prophylactically or therapeutically ablate glandular tissue in a breast. The frequency of the applied microwave is between 100 MHz and 3000 MHz, e.g., or between 200 MHz and 2000 MHz, 500 MHz and 1500 MHz, 850 MHz and 1050 MHz, or 902 and 928 MHz, e.g., 915 MHz.

If the breast tissue containing glandular tissue is larger than the effective heating zone, the procedure can be repeated until all the glandular tissue has been ablated.

Breast tissue is heated until substantially all of the water-rich glandular tissue in the irradiated zone is destroyed. Typically this will involve heating to a predetermined temperature for a specified amount of time, e.g., to 43° C. for 60 minutes. Heating to higher temperatures will reduce the amount of time needed to kill cells. It is known that the amount of time to kill tumor cells decreases by a factor of two for every degree of increase in temperature above 43° C. Thus, a 60 minute treatment of tumor cells at 43° C. can be, but need not be, reduced to about 7.5 minutes by raising the temperature to 46° C.

When microwave radiation is used therapeutically, microwaves are applied to ablate substantially all of the glandular tissue of the breast, including non-tumorous as well as tumorous tissue. The microwave therapies can be used in conjunction with other treatment modalities, such as chemotherapy, radiation, or lumpectomy.

The invention will be further described in the following examples, which do not limit the scope of the invention described in the claims.

EXAMPLES

The following examples illustrate the use of microwaves to selectively ablate glandular tissue in a breast.

Example 1

Generation of focused microwave fields in samples simulating a mixture of glandular and fatty tissue The ability of a parallel microwave antennae array to generate a focused microwave field was determined using a Celsion Microfocus 1000 system (Celsion Corporation, Columbia, Md.) on simulated tissue samples. The samples included various combinations of fat (simulated with CRISCO™ shortening, Proctor & Gamble) and water-rich (96% fat-free hamburger) substances to simulate fatty tissue and glandular tissue, respectively. The CRISCO™ shortening and hamburger were mixed thoroughly. Samples included 100% lean hamburger, 66.6% lean hamburger/33.3% CRISCO™ shortening, 50% lean hamburger/50% CRISCO™ shortening, and 100% CRISCO™ shortening.

The samples were placed in a refrigerator overnight, after which they were individually removed and heated with a phased-array hyperthermia system (Microfocus 1000, Celsion, Columbia, Md.). The samples were encased in a plastic bottle less than 6 cm thick to allow placement between the antennae of the system. Following application of microwaves of 915 MHz, the temperature in the heating zone was recorded, along with the applied power in order to determine the amount of power required to raise the sample temperature to 46° C.

Figure 3A:
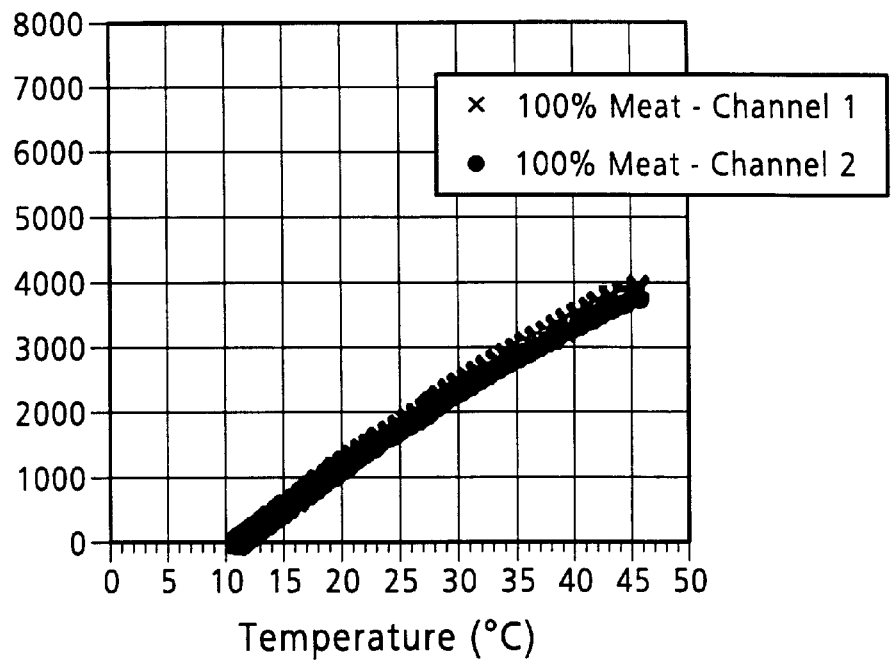
FIGS. 3A–3D are graphs showing the amount of power required to heat samples containing varying amounts of water-rich and fat-rich tissue to 46° C.
Figure 3B:
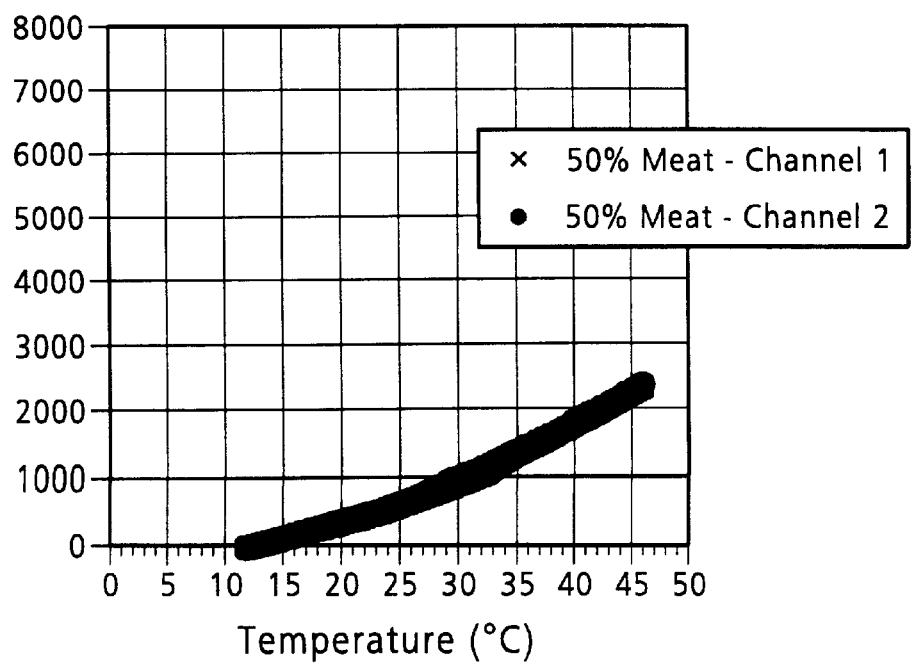
Figure 3C:
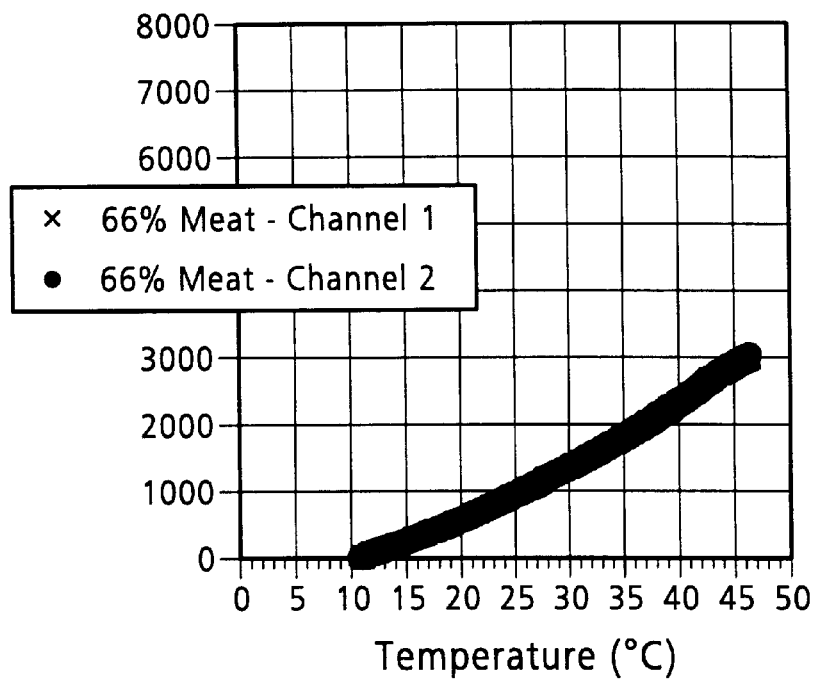
Figure 3D:
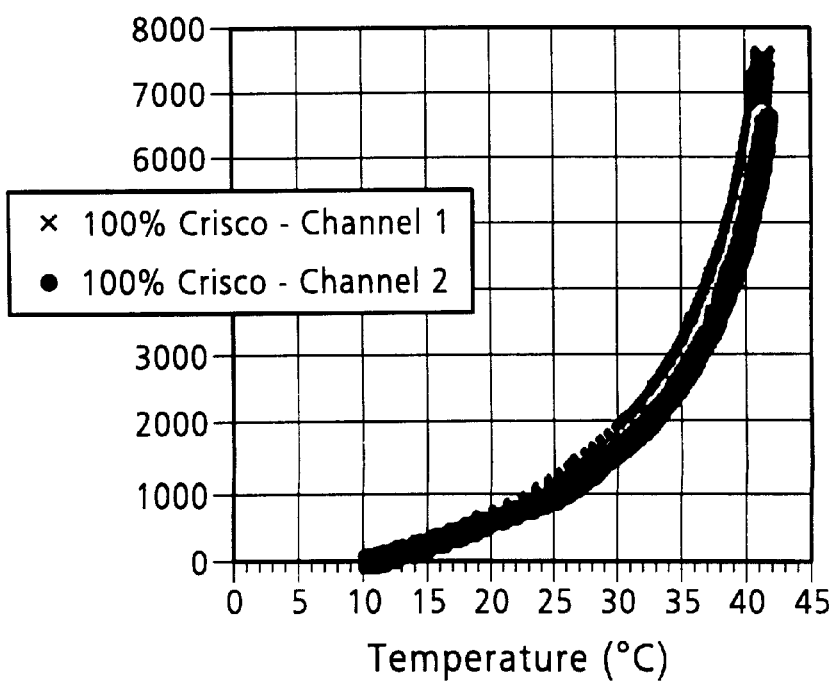

The results of these studies are shown in the graphs of FIGS. 3A–D. In these graphs, the ordinate shows applied power (watt-minutes) while the abscissa shows the measured temperature of the sample. 4000 heat units were required to reach 46° C. with pure hamburger (FIG. 3A). 2000 heat units were required to reach 46° C. for the sample having 50% hamburger/50% CRISCO™ shortening (FIG. 3B), and 3000 heat units were required to reach 46° C. for the sample having 66% hamburger/33% CRISCO™ shortening (FIG. 3C). For the sample with 100% CRISCO™ shortening, the temperature failed to reach 46° C., even after the application of more than 7000 heat units (FIG. 3D). These results suggest that differential heating can be used to selectively ablate water-rich tissue such as the glandular tissue in preference to fat-rich tissues.

To directly compare temperature changes within a phantom in simulated glandular, adipose, and skin tissues, a 96% hamburger/4% CRISCO™ shortening phantom was irradiated in a Celsion 1000 APA apparatus and TEM1 applicators. Probes were inserted in the following locations in the phantom to measure temperature changes: T1 and T2, surface (simulating skin); T3, hamburger, (simulating glandular tissue); and T4 and T5, CRISCO™ shortening (simulating adipose tissue).

The temperature was measured at each probe T1–T5 before and after application of focused microwaves at 915 MHz for 60 seconds. The temperature increase in simulated glandular tissue relative to simulated adipose tissue was determined by dividing the increase in temperature at probe T3 by the increase in temperature of T4 (dT3/dT4) or T5 (dT3/dT5).

Figure 4:
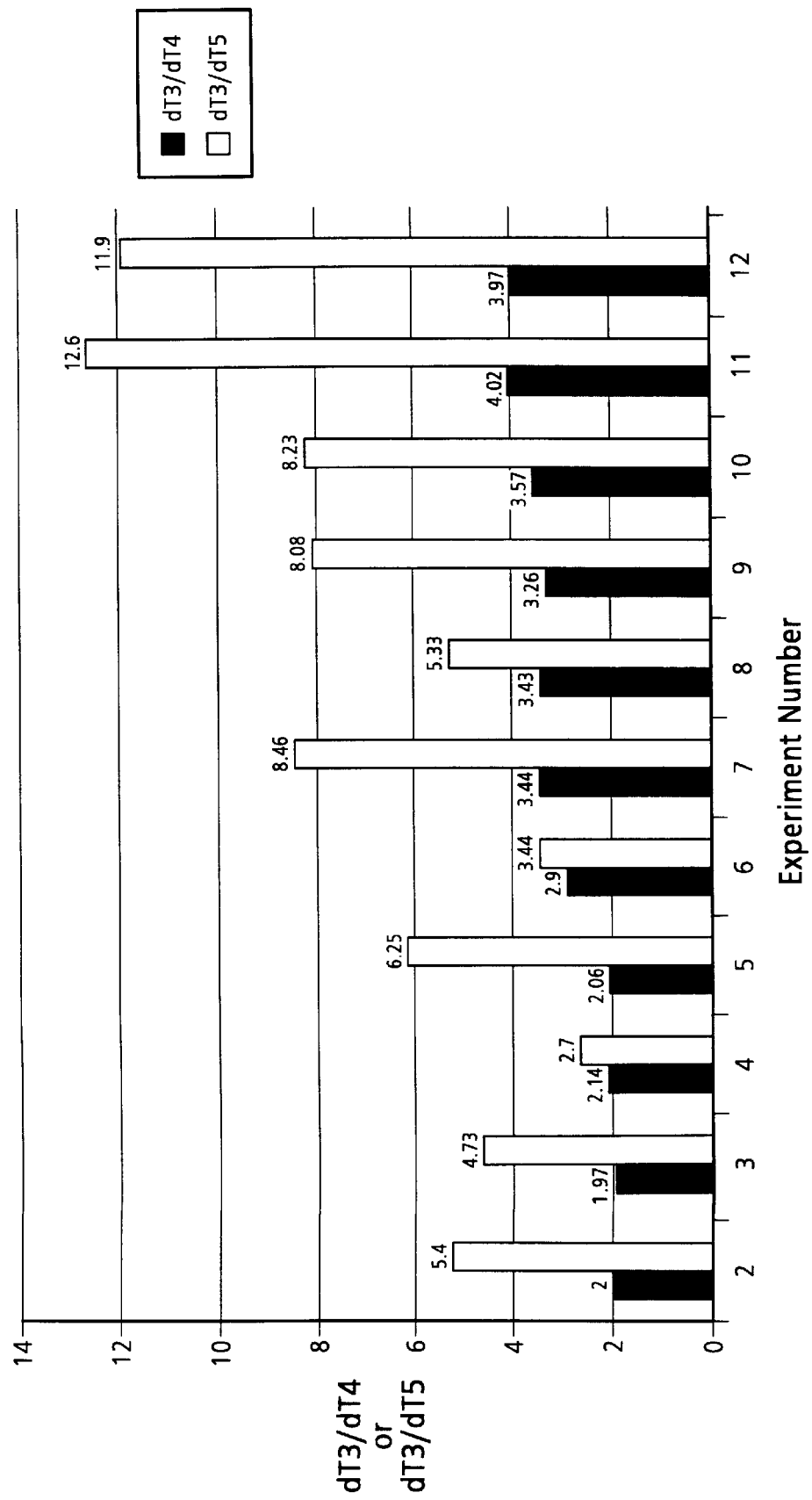
FIG. 4 is a histogram showing the temperature increase in simulated glandular tissue relative to adipose tissue in eleven applications of microwave radiation.

FIG. 4 shows a bar graph of ratios corresponding to dT3/dT4 and dT3/dT5 for 11 separate applications of focused microwaves to the phantom, which are labeled experiments 2–12. The first trial was conducted to verify that the probes measured temperature accurately. Thus, data are not shown for this trial. The microwaves were focused just before beginning each trial. For dT3/dT4, the relative temperature increase in simulated glandular tissue compared to simulated adipose tissue ranged from 1.97 to 4.07. For dT3/dT5, the relative temperature increase was from 2.7 to 12.6. The difference in observed ratios for dT3/dT4 and dT3/dT5 is attributed to differences in beginning temperatures at probes T4 and T5.

Figure 5:
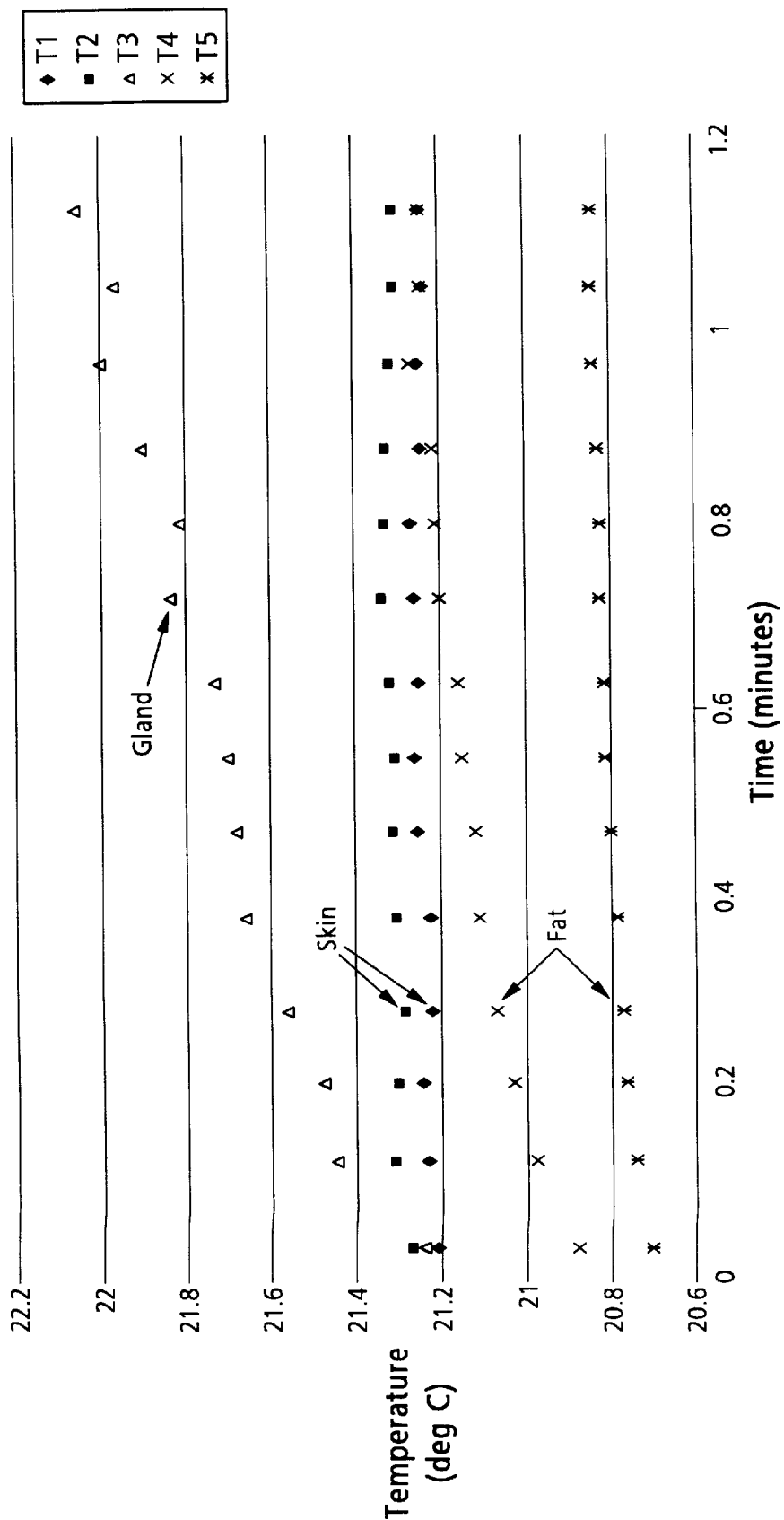
FIG. 5 is a graph showing the temperature increase with time in five different regions of a breast phantom following application of microwave radiation.

The temperature change over time at each of the five probes T1–T5 for trial 2 is shown in FIG. 5. Temperature changes were measured in 0.1 minute intervals for a total of 1.2 minutes. The temperature of the simulated glandular tissue (T3) increased from 21.2° C. to about 22.0° C., while the temperature of simulated adipose tissue increased from about 20.8° C. to 21.2° C. (T4), and from about 20.7° C. to 20.8° C., respectively (T5). The temperature of simulated skin remained at about 21.2° C. for the duration of the experiment (T1 and T2).

These results demonstrate that upon application of focused microwave radiation, the temperature of simulated glandular tissue increases at a higher rate than the temperature of simulated adipose tissue. These data further indicate that ductal, glandular and tumor tissues deep within the breast will heat rapidly and will reach high temperatures, sufficient to ablate these tissues, much faster than surrounding fatty breast tissue. In addition, the data indicate that the surface temperature of the breast should remain relatively constant in these conditions.

Example 2
Identification of heating patterns in breast tissue following irradiation with microwaves To estimate the heating pattern in breast tissue exposed to microwave radiation, a virtual, computer simulation was performed in which three-dimensional specific absorption rate (SAR) heating patterns were calculated using finite-difference time-domain theory and computer simulations. The modeling was performed assuming dimensions for dual-opposing TEM2 applicators (Celsion, Columbia, Md.) operating at 915 MHz with the applicators coherently combined to focus a radiated beam at a central position in 6 cm thick homogeneous fatty breast tissue. The breast tissue was modeled assuming a dielectric constant of 12.5 and electrical conductivity was 0.21 Siemens/meter.

In the virtual model, each applicator was located on the side walls of the container enclosing the phantom, and the container was modeled as a high dielectric constant material that is used to match and shape the radiation inside the waveguide aperture. The model also included a virtual sheet of plexiglass placed adjacent to each applicator and parallel to the waveguide aperture, and a 6 cm thick homogeneous fatty breast phantom was inserted between the two applicators, with air a model of air occupying the remaining volume.

An SAR was calculated by squaring the electric field amplitude and multiplying by the electrical conductivitity of the tissue. SAR is often described in levels of 50%, to indicate the region in which the SAR is greater than or equal to 50% of the maximum value, and 75%, to indicate the region in which the SAR is greater than or equal to 75% of the maximum value. The SAR is proportional to initial rise in temperature per unit time, ignoring blood flow and thermal conduction.

Figure 6A:
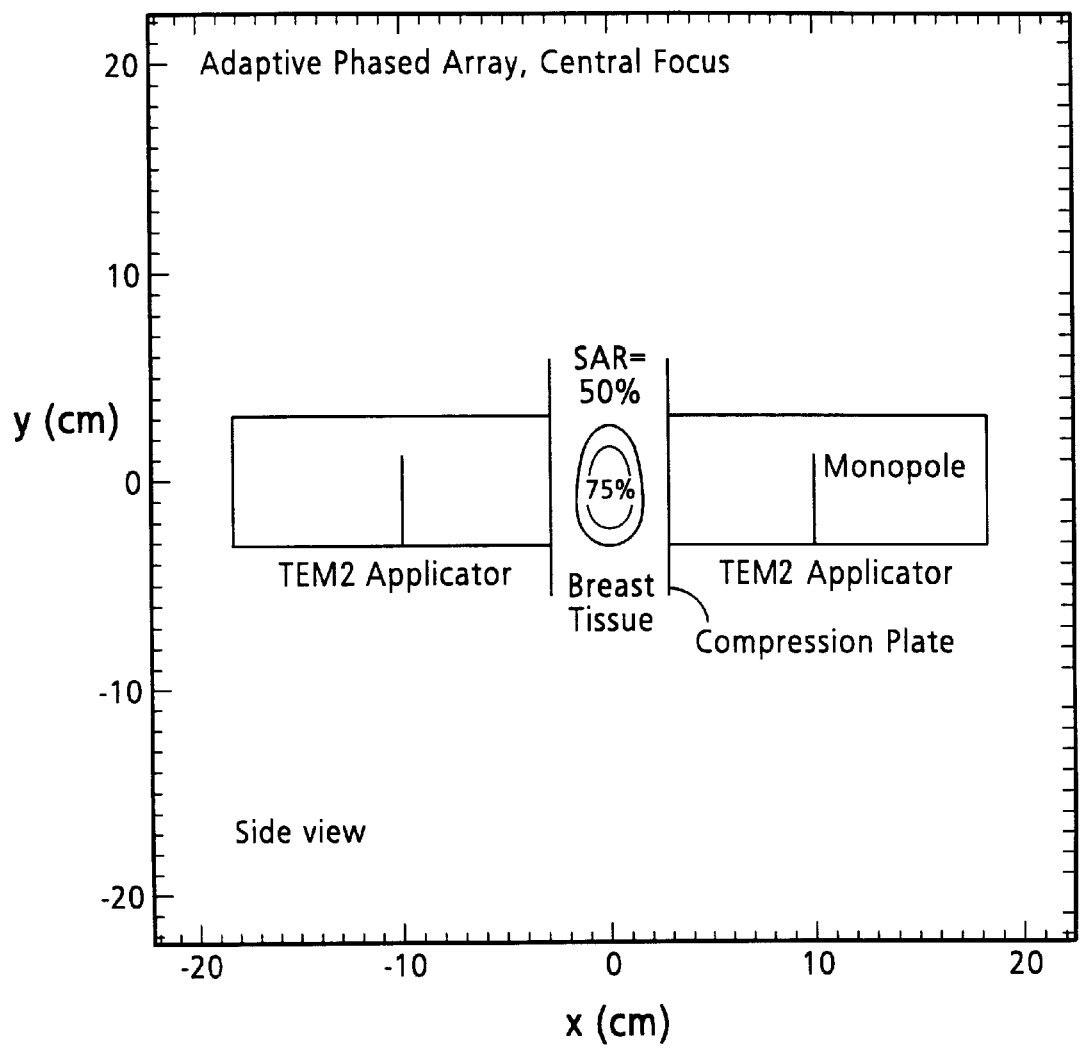
FIGS. 6A–6C are graphs showing the specific absorption rate (SAR) 50% and 75% contour heating patterns calculated for homogenous breast tissue subjected to ultraviolet radiation using an adaptive phased array and microwave applicators. The graphs shown are in the xy (FIG. 6A), xz (FIG. 6B), and yz (FIG. 6C) planes.
Figure 6B:
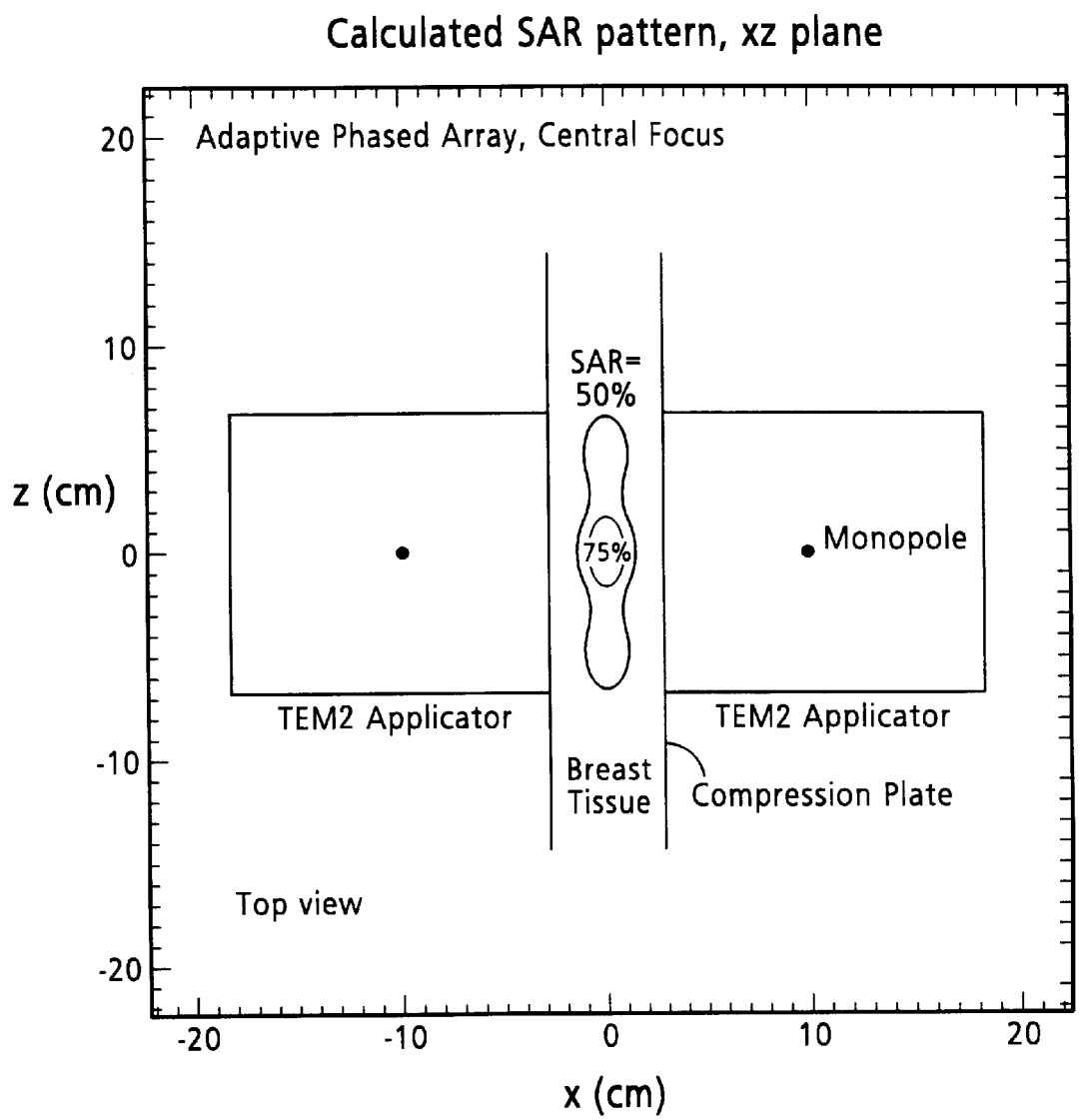
Figure 6C:
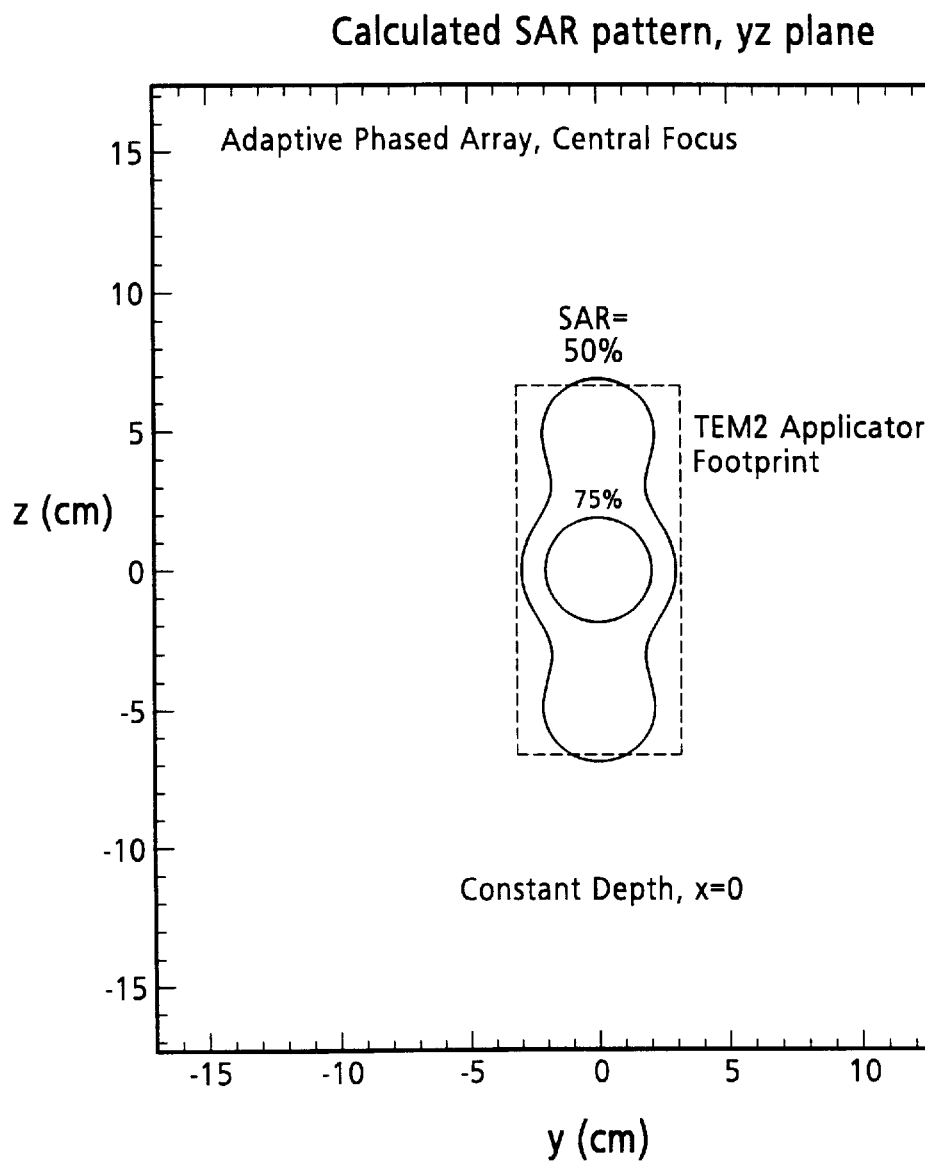

SAR patterns were computed in three principal planes (xy, xz, and yz) as shown in FIGS. 6A–C. The pattern is generally bell shaped and centered between the applicators.

The xy plane, z=0, is shown in FIG. 6A. FIG. 6B shows the top view (xz plane, y=0) of the SAR pattern (75% and 50% contours). The pattern exhibits a small elliptically shaped 75% SAR region surrounded by a three-lobe shaped elliptical 50% SAR region. FIG. 6C shows the end view (yz plane, x=0) of the SAR pattern (75% and 50% contours). The pattern exhibits a small circularly shaped 75% SAR region surrounded by a three-lope shaped elliptical 50% SAR region.

Example 3
Selective microwave ablation of glandular tissue in vivo

To demonstrate that microwave radiation selectively ablates water-rich tissues in vivo, rabbits bearing leg tumors were irradiated with microwave radiation in the region of the popliteal fossa.

Both water-rich structures such as lymph nodes and tumorous tissues, and adipose tissue are found in this region.

Tissues were heated to 46° C. for 8 minutes with microwaves of 915 MHz using Celsion TEM1 applicators. Histological examination following application of 915 MHz microwave radiation revealed that the water-rich tissues, including tumorous tissues, were all damaged or destroyed by heating, while the fat cells appeared unaffected. These results demonstrate that water-rich tissue can be ablated while adjoining fat tissue is unaffected.

Other Embodiments

It is to be understood that while the invention has been described in conjunction with the detailed description thereof, the foregoing description is intended to illustrate and not limit the scope of the invention, which is defined by the scope of the appended claims. Thus, the invention includes, e.g., a method of selectively destroying water-rich tissues in a body part that includes both water-rich tissue and fatty tissue. A region of the body part can be irradiated with microwave energy at a wavelength and for a time sufficient to heat the water-rich tissues but not the fatty tissue to a temperature that destroys the water-rich tissue.

Other aspects, advantages, and modifications are within the scope of the following claims.

What is claimed is:

1. A method for preventing the development of a breast tumor in an individual, the method comprising:
   (a) identifying an individual at risk for developing a breast tumor; and
   (b) irradiating with microwave radiation a region of the breast at risk for developing the tumor at a wavelength and for a time sufficient to heat glandular tissue but not fatty tissue to a temperature of at least about 43° C., thereby preventing the development of a breast tumor.

2. The method of claim 1, wherein said microwave radiation forms a focused field in said tissue.

3. The method of claim 1, wherein said individual lacks a detectable tumor in said tissue.

4. The method of claim 1, wherein said microwave radiation is between 100 and 1000 Mhz.

5. The method of claim 1, wherein said microwave radiation is between 500 and 1000 Mhz.

6. The method of claim 1, wherein said microwave radiation is between 902 and 928 Mhz.

7. The method of claim 1, wherein said microwave radiation is 915 MHz.

8. The method of claim 1, wherein the temperature is about 46° C.

9. The method of claim 1, wherein the temperature of skin of the breast overlying the irradiated region does not change following microwave irradiation.

10. A method for selectively ablating glandular breast tissue, the method comprising
   irradiating with microwave radiation a region of the breast containing both glandular and fatty tissues at a wavelength and for a time sufficient to heat glandular tissue but not fatty tissue to a temperature of at least about 43° C., thereby selectively ablating glandular tissue.

11. The method of claim 10, wherein said glandular tissue includes tumorous tissue.

12. The method of claim 10, wherein said glandular tissue lacks any detectable cancerous breast tissue.

13. The method of claim 10, wherein said microwave radiation forms a focused field in said tissue.

14. The method of claim 10, wherein said individual lacks a detectable tumor in said tissue.

15. The method of claim 10, wherein said microwave radiation is between 100 and 1000 Mhz.

16. The method of claim 10, wherein said microwave radiation is between 500 and 1000 Mhz.

17. The method of claim 10, wherein said microwave radiation is between 902 and 928 Mhz.

18. The method of claim 10, wherein said microwave radiation is 915 MHz.

19. The method of claim 10, wherein the temperature is heated to about 46° C.

20. The method of claim 10, wherein the temperature is heated to about 46° C.

* * * * *